(12) United States Patent
Chandler

(10) Patent No.: US 12,161,811 B2
(45) Date of Patent: Dec. 10, 2024

(54) HEAT AND MOISTURE EXCHANGE DEVICES

(71) Applicant: SMITHS MEDICAL INTERNATIONAL LIMITED, Ashford (GB)

(72) Inventor: Martin Chandler, Ashford (GB)

(73) Assignee: ICU MEDICAL INTERNATIONAL LIMITED, Ashford (GB)

( * ) Notice: Subject to any disclaimer, the term of this patent is extended or adjusted under 35 U.S.C. 154(b) by 920 days.

(21) Appl. No.: 16/302,254

(22) PCT Filed: May 15, 2017

(86) PCT No.: PCT/GB2017/000073
§ 371 (c)(1),
(2) Date: Nov. 16, 2018

(87) PCT Pub. No.: WO2017/216508
PCT Pub. Date: Dec. 21, 2017

(65) Prior Publication Data
US 2019/0275282 A1    Sep. 12, 2019

(30) Foreign Application Priority Data

Jun. 18, 2016 (GB) .................................... 1610715

(51) Int. Cl.
*A61M 16/10* (2006.01)

(52) U.S. Cl.
CPC . *A61M 16/1045* (2013.01); *A61M 2205/3633* (2013.01)

(58) Field of Classification Search
CPC .......... A61M 16/0465; A61M 16/1045; A61M 2205/3633

USPC ...................................................... 128/201.13
See application file for complete search history.

(56) References Cited

U.S. PATENT DOCUMENTS

| 3,881,482 A * | 5/1975 | Lindholm ......... A61M 16/1045 128/201.13 |
| 5,595,173 A * | 1/1997 | Dodd, Jr. .............. A62B 9/003 128/201.13 |
| 2004/0123974 A1* | 7/2004 | Marler .............. A61M 16/1055 165/9.4 |

FOREIGN PATENT DOCUMENTS

| EP | 0409402 A1 * | 1/1991 | ........ A61M 16/1045 |
| EP | 0579384 A1 | 1/1994 | |
| GB | 2237208 A | 5/1991 | |
| WO | 9715344 A1 | 5/1997 | |
| WO | 20120033421 A1 | 3/2012 | |
| WO | WO-2012033421 A1 * | 3/2012 | ........ A61M 16/0808 |
| WO | WO-2015052681 A1 * | 4/2015 | ........ A61M 16/0066 |

OTHER PUBLICATIONS

PCT International Search Report and Written Opinion, PCT/GB2017/000073 EPO Jul. 20, 2017.

* cited by examiner

*Primary Examiner* — Elliot S Ruddie
(74) *Attorney, Agent, or Firm* — Louis Woo

(57) ABSTRACT

An HME has a housing (10) moulded in two parts (26 and 27) of a thick, thermally-insulative foamed plastics to form an enlarged central region (13) and opposite end walls (24 and 25). Separate patient and machine end couplings (11 and 12) are bonded to openings (37 and 47) in the end walls. The two housing parts (26 and 27) are bonded end to end about an HME element (14) formed by a strip of treated corrugated paper wound about a support sleeve (50).

18 Claims, 2 Drawing Sheets

HEAT AND MOISTURE EXCHANGE DEVICES

This invention relates to HME devices of the kind having a housing providing an inlet, an outlet and a transversely enlarged region between the inlet and outlet, the device including an HME element located in the enlarged region.

Where a patient breathes through a tube inserted in the trachea, such as a tracheostomy or endotracheal tube, gas flow to the bronchi is not warmed and moistened by passage through the nose. Unless the gas is warmed and moistened in some way it can cause damage and discomfort in the patient's throat. The gas can be conditioned by a humidifier in the ventilation circuit but, most conveniently, a heat and moisture exchange device (HME) is used. HMEs are small, lightweight devices including one or more exchange elements, such as of a paper or foam treated with a hygroscopic substance. When the patient exhales, gas passes through the exchange element and gives up a major part of its heat and moisture to the element. When the patient inhales, gas passes through the exchange element in the opposite direction and takes up a major part of the heat and moisture in the exchange element so that the gas inhaled by the patient is warmed and moistened. These HMEs are low cost and disposable after a single use. They can be connected in a breathing circuit or simply connected to the machine end of a tracheal tube and left open to atmosphere where the patient is breathing spontaneously. HMEs can be used with other breathing devices such as face masks.

HMEs are sold by Smiths Medical International Limited of Ashford, Kent, England under the Thermovent name (Thermovent is a registered trade mark of Smiths Medical International Limited), by Hudson RCI AB under the TrachVent name (TrachVent is a registered trade mark of Hudson RCI AB), by DAR, Medisize, Intersurgical and other manufacturers. Examples of HMEs are described in GB2391816, WO01/72365, U.S. Pat. No. 5,505,768, SE516666, U.S. Pat. No. 3,881,482, DE20302580, DE20114355U, WO97/01366, US2002/0157667, U.S. Pat. No. 6,422,235, EP1208866, U.S. Pat. No. 4,971,054, EP1699515, U.S. Pat. No. 5,035,236, EP535016, U.S. Pat. No. 5,647,344, GB2267840, EP856327, EP1699515, U.S. Pat. No. 7,363,925, WO15/107320, US2008/0099013 and GB1511401.0. The "Thermovent T" HME sold by Smiths Medical has a T-shape configuration with two HME elements mounted at opposite ends of a straight tubular housing extending transversely of the connection port by which the device is fitted onto a tracheostomy tube or the like. The tubular housing for the HME elements may be curved to follow the anatomical profile of the neck, as described in EP1888157.

Although HMEs can be quite efficient they are not yet as effective in humidifying as active humidifiers including a heater and water supply and, for this reason, some clinicians do not use HMEs for patients with severe respiratory problems. There is, therefore, still a need to increase the efficiency of HMEs so that they can be used more widely.

It is an object of the present invention to provide an alternative HME device.

According to the present invention there is provided an HME device of the above-specified kind, characterised in that the wall of the housing at least in the enlarged region includes a major part of its thickness of a foamed plastics material such as to provide thermal insulation of the housing around the HME element.

The foamed plastics material preferably has a thermal conductivity of substantially 0.03 W/(m·K) or less and the ratio of the wall thickness of the enlarged region to its external diameter is substantially 1:8. The inlet and outlet are preferably axially aligned with one another. The enlarged region preferably includes a cylindrical portion of circular section and two opposite end wall portions extending laterally to the inlet and outlet respectively. Both the cylindrical portion and the wall portions may be of a foamed plastics material through a major part of their thickness. At least the inner surface of the opposite end wall portions preferably extend at an angle to the normal to the axis of HME device. The inlet and outlet may be components formed separate from the enlarged region and attached with the enlarged region. The HME element is preferably a coil of corrugated paper. The coil of corrugated paper may be wound about a hollow tubular sleeve. The housing may be formed in two parts joined together at mating end surfaces in the enlarged region. The mating end surfaces may be are inclined in opposite senses at an angle to the normal to the axis of the device. Opposite end surfaces of the HME element may each form a shallow, concave, conical shape.

Two embodiments of HME devices according to the present invention will now be described, by way of example, with reference to the accompanying drawings, in which.

Figure 1:
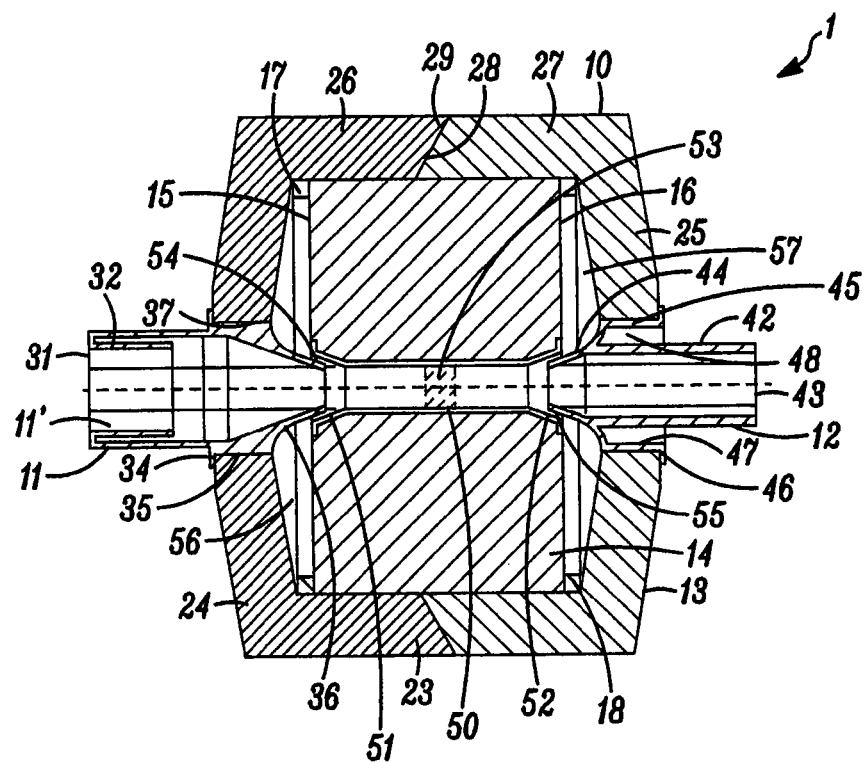
FIG. 1 is a cross-sectional side elevation view of the first embodiment HME device.
Figure 2:
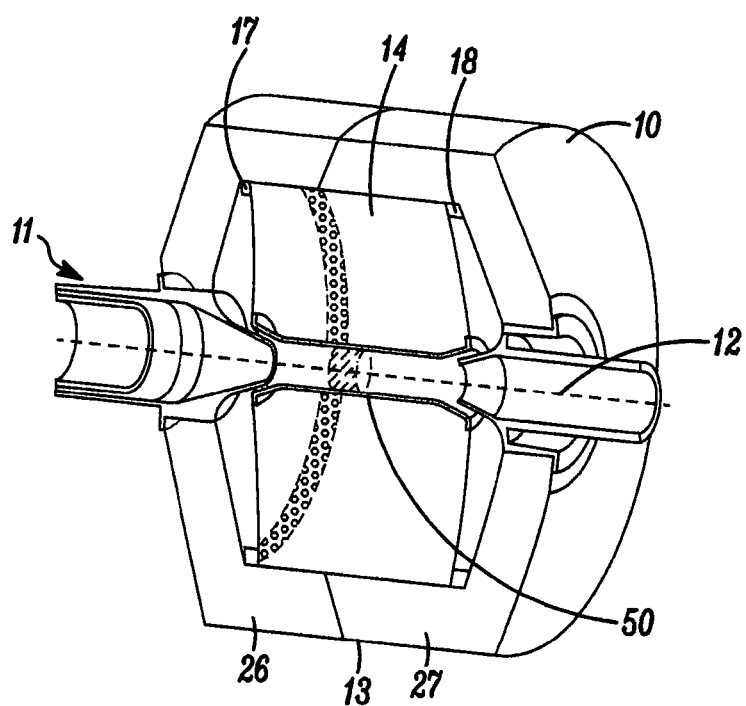
FIG. 2 is a perspective, cut-away, cross-sectional view of HME of FIG. 1.

With reference first to FIGS. 1 and 2 there is shown an HME device 1 having an outer housing 10 of circular section with a patient end coupling or inlet 11 having a luer tapered inner surface 11' adapted to fit onto a mating male connector at the end of a breathing device (not shown) such as an endotracheal or tracheostomy tube. At the opposite end of the device 1 a machine end coupling or outlet 12 is axially aligned with the patient end coupling 11. Between the patient end coupling 11 and the machine end coupling 12 the housing 10 has a transversely or radially enlarged central region 13. The central region 13 of the housing 10 contains an HME element 14 in the form of a strip of corrugated paper treated with a hygroscopic salt to promote the absorption of moisture, the strip being wound into a circular coil. The corrugations of the paper strip are aligned parallel with the axis of the device so that air can flow along them. The patient face 15 and machine face 16 of the element 14 are spaced slightly from the housing 10 in the central region 13 so that air can flow through the element across the entire surface of both faces. The HME element 14 is supported on opposite sides in the housing 10 by two annular rings 17 and 18 of a compressible plastics material.

The central region 13 of the housing 10 is formed separately of the patient end coupling 11 and the machine end coupling 12. The major part of the length of the central region 13 is provided by a cylindrical portion 23 of circular section and constant diameter along its length. At opposite ends, the central region 13 has respective end walls 24 and 25 extending transversely inwards at a shallow angle to the normal to the axis of the HME so that at least the inner surface of the walls slopes at a shallow angle to the normal. The central region 13 is moulded in two parts 26 and 27 that are subsequently bonded together about the HME element 14. The two parts 26 and 27 are bonded together at mating end surfaces 28 and 29 respectively that are inclined in opposite senses to a normal to the axis of the HME at an angle of about 45°. The two parts 26 and 27 are moulded from the same thermally-insulative, rigid foamed plastics material such as expanded polyurethane foam. This material has a thermal conductivity of 0.03 W/(m·K). Preferably any alternative insulating material should have a similar or lower conductivity. The walls of the two parts 26 and 27 are relatively thick compared with conventional HMEs being about 12 mm for an HME having an external diameter of about 102 mm so that the ratio of the wall thickness to diameter is about 1:8. The walls of the two parts are preferably of the foamed material through their entire thickness although they could be provided with a non-foamed layer or skin on the inner, outer or both surfaces.

The patient end coupling 11 is a one-piece integral moulding of a rigid (non-foamed) plastics material, such as nylon, of generally cylindrical shape and circular section. The patient end 31 of the coupling 11 is formed with an in-turned sleeve 32 the inner surface 11' of which is tapered and is adapted provide a female coupling for fitting on the outside of a conventional 15 mm male coupling (not shown) attached to a breathing tube or the like. About half way along the coupling 11 a shallow flange 34 projects radially outwardly and abuts the outer surface of the patient end wall 24 of the central section 13. The part of the coupling 11 on the machine side of the flange 34 is divided into a slightly enlarged cylindrical section 35 and a tapered nose section 36. The cylindrical section 35 is a close fit in a central opening 37 in the patient end wall 24 where it is bonded in position such as with an adhesive or solvent. The nose section 36 tapers internally and externally to a reduced diameter at its machine end.

The machine end coupling 12 is also a one-piece moulding shaped to provide a male tapered connection and, in this respect includes a cylindrical spigot 42 of circular section having a constant internal diameter and an external diameter tapering along its length, reducing in diameter towards the free, machine end 43 of the coupling. The spigot 42 is supported at its opposite, patient end where it joins with a tapering nose portion 44 projecting inwardly of the housing 10. The machine end coupling 12 is completed by an integral cylindrical outer sleeve 45 projecting axially outwardly from the nose portion 44 around the spigot 42 along about one half its length. The outer sleeve 45 is terminated by a narrow, outwardly-projecting flange 46 and is a close fit within a central opening 47 in the machine end wall 25 into which it is bonded, with the flange abutting the outside surface of the wall around the opening. The inner surface of the outer sleeve 45 and the outer surface of the spigot 42 extending with the sleeve are spaced from one another to form an annular recess 48 into which the forward end of a mating female coupling (not shown) can be received.

The HME element 14 is a coil of treated corrugated paper wound into an annular form about a hollow tubular sleeve 50 extending axially through the element between its opposite ends. The sleeve 50 is flared outwardly at opposite ends 51 and 52 to form enlarged, tapering openings into the sleeve. The sleeve 50 is blocked midway along by a valve 53, such as a duckbill valve, that can be opened by extending a suction catheter along the sleeve.

The nose 36 of the patient end coupling 11 and the nose 44 of the machine end coupling 12 project a short distance into the respective flared ends 51 and 52 of the sleeve 50 but leave a space between the outside of each nose and the inside of the respective flared end to provide respective annular gas flow passages 54 and 55 around the outside of the noses. The passages 54 and 55 open into respective annular cavities 56 and 57 defined by the outer surface of the noses 36 and 44 of the couplings 11 and 12, the respective end face 15 and 16 of the HME element 14 and the inside surface of a sloping end walls 24 and 25 of the central section 13.

In use, the patient end coupling 11 is fitted on to a coupling at the machine end of a breathing device, such as a tracheal tube or face mask. When the patient exhales, warm, moist air flows forwardly through the coupling 11 and out of the end of the nose portion 36 into the patient end of the sleeve 50. Further flow forwardly is prevented by the valve 53 so the air instead flows rearwardly through the annular passage 54 into the cavity 56 where the air is dispersed evenly over the rear-facing face 15 of the HME element 14. The even distribution is aided by the width of the cavity 56 and the slope on the end wall 24. The air then flows through the HME element 14 along the spaces around the corrugations and between adjacent turns of the coil. As it does this the air gives up a large part of its heat and moisture to the HME element 14. The air then emerges from the forward-facing face 16 of the element 14 into the machine end cavity 57 from where it changes direction and flows rearwardly through the annular passage 55 into the machine end of the sleeve 50. Further flow in the same direction is blocked by the valve 53 so the air reverses direction to flow forwardly out along the bore of the machine end coupling 12.

When the patient inhales, or when air is supplied by a ventilator or the like in the opposite direction, the air follows the same path through the device 1 but in the opposite direction. The inhaled air is cooler and drier than the exhaled air so, as this passes through the HME element 14, it takes up the major part of the warmth and moisture absorbed in the element during the previous exhalation phase thereby warming and moistening the air that flows to the patient.

The thickness and the thermally-insulative nature of the foamed material from which the wall of the central region 13 of the housing 10 is made help maintain the interior of the HME 1 at a stable temperature closer to body temperature than conventional HMEs during both exhalation and inhalation. This has been found to increase the efficiency of the HME compared with conventional HMEs. This increase in efficiency brings the performance of the HME closer to that of active humidifiers and thereby makes the HME a more viable alternative where a high level of warming and humidification is required. The lower cost, ease of use, the absence of any requirement for power or water supply are considerable advantages. The HME device can be disposed of after a single use, thereby avoiding the infection risk and cleaning requirements of active humidifiers.

Figure 3:
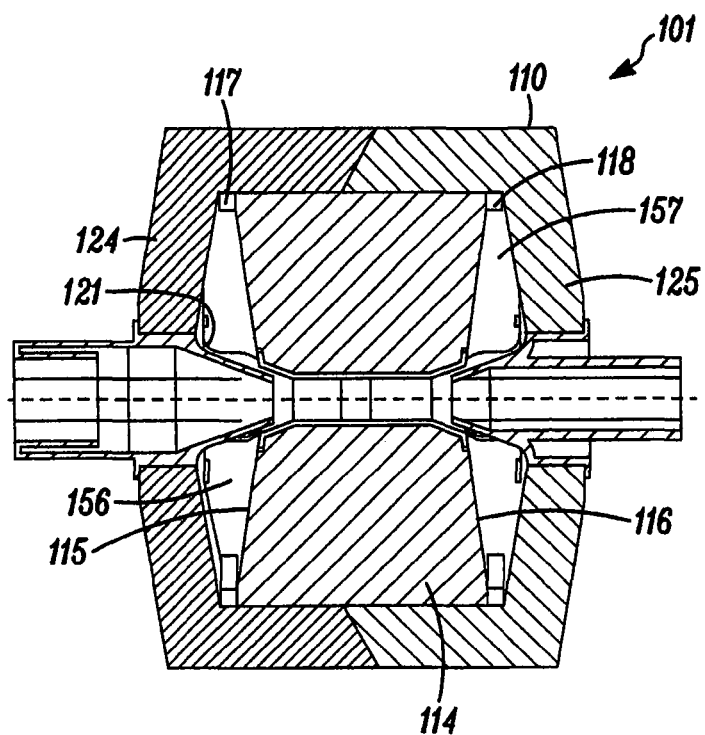
FIG. 3 is a cross-sectional side elevation view of the second embodiment HME.
Figure 4:
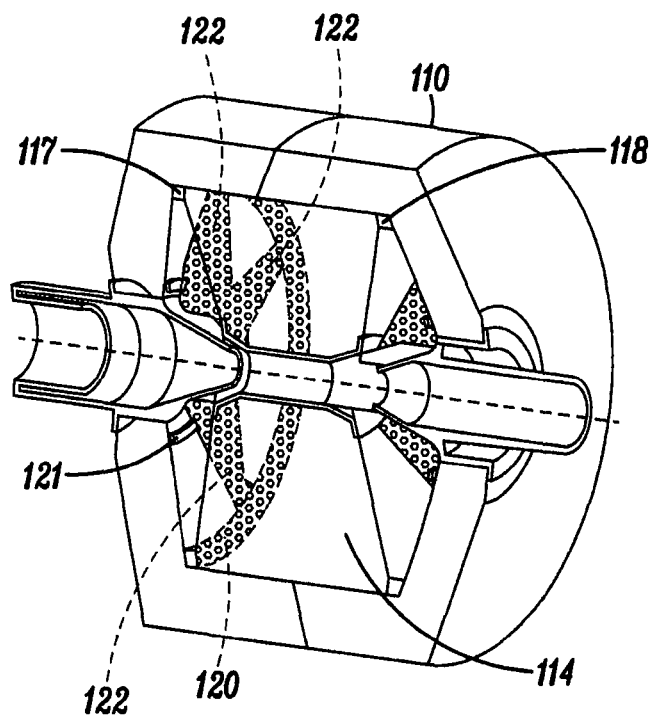
FIG. 4 is a perspective, cut-away, cross-sectional view of the HME of FIG. 3.

Various modifications within the scope of the present invention are possible to the HME described with reference to FIGS. 1 and 2. Although the HME element 14 is described as having flat end surfaces 15 and 16 it would be possible for the element to have alternative configurations as, for example shown in FIGS. 3 and 4. The HME 101 shown in FIGS. 3 and 4 is similar to that shown in FIGS. 1 and 2 with an identical housing 110 but where the HME element 114 differs by having opposite end surfaces 115 and 116 of a shallow, concave, conical shape forming an included angle of about 160°. The simple annular rings used to support the HME element in the housing in the embodiment of FIGS. 1 and 2 are replaced in the second embodiment with wheel-like supports 117 and 118. The supports 117 and 118 each having a circular outer rim 120 located between the outer edge of the respective end face 115 and 116 and the adjacent end wall 124 and 125. Each support 117 and 118 also has a central hub 121 extending around the outside of the nose portion of the respective coupling and attached with the respective rim by eight radially extending vanes 122. The vanes 122 are spaced evenly around each support wheel 117 and 118 and taper in height along their length from the hub 121 where they are relatively high to the outer rim 120 where they are relatively small. The shape of the vanes 122 is such as to conform to the shape of the cavity 156 and 157 between the end faces 115 and 116 of the HME element 114 and the facing sloping end walls 124 and 125 of the housing 110. The edges of the vanes 122 contact the end face 115 and 116 of the HME element 114 and the inside of the facing end wall 124 and 125. This configuration provides a cavity 156 and 157 with an increased volume and this, together with the channelling effect of the vanes 122, may lead to a more even distribution of gas over the end face 115 and 116 of the HME element 114, which in turn, helps maintain the efficiency of the HME for a longer period.

The HME element need not be made of a coil of corrugated, treated paper but could be of other materials used in conventional HME elements, such as foam or hollow fibres. It is not essential that the HME device and HME element be circular in section since they could be of other shapes such as oval or rectangular, although the circular shape has been found to give the highest efficiency. Although the HMEs described above have folded air flow paths at both ends, it would be possible instead for an HME element to extend across the entire width of the housing and for the inlet and outlet to open onto the centre of the end faces of the element. Although the HMEs described above have an axial form where the inlet and outlet are axially aligned, the thermally-insulating housing of the present invention may also benefit HMEs having other conventional alternative configurations such as a T-shape configuration with two HME elements mounted at opposite ends of a straight tubular housing extending transversely of the connection port by which the device is fitted onto a tracheostomy tube or the like.

The invention claimed is:

1. A heat and moisture exchange (HME) device comprising a housing providing an inlet coupling, an outlet coupling and a transversely enlarged central region between the inlet and outlet couplings, the device including an HME element retained in the enlarged central region having opposite end faces spaced from respective inner opposing walls of the housing in the enlarged central region of the housing so that air can flow through the element across the entire surface of both faces, characterized in that a wall of the housing at least in the enlarged central region includes foamed plastic material having a thickness adapted to provide thermal insulation of the housing around the HME element.

2. An HME device according to claim 1, characterised in that the foamed plastics material has a thermal conductivity of substantially 0.03 W/(m·K) or less.

3. An HME device according to claim 1, characterised in that the ratio of the wall thickness of the enlarged central region to an external diameter of the foamed plastics material is substantially 1:8.

4. An HME device according to claim 1, characterised in that the inlet and outlet are axially aligned with one another.

5. An HME device according to claim 1, characterised in that the enlarged central region includes a cylindrical portion of circular section and two opposite end wall portions extending laterally to the inlet and outlet respectively.

6. An HME device according to claim 5, characterised in that both the cylindrical portion and the wall portions are of the foamed plastics material through the major part of their thickness.

7. An HME device according to claim 5, characterised in that at least an inner surface of the opposite end wall portions extend at an angle to the normal to an axis of the HME device.

8. An HME device according to claim 1, characterised in that the inlet coupling and outlet coupling are components formed separate from the enlarged central region and attached with the enlarged central region.

9. An HME device according to claim 1, characterised in that the HME element is a coil of corrugated paper.

10. An HME device according to claim 9, characterised in that the coil of corrugated paper is wound about a hollow tubular sleeve.

11. An HME device according to claim 1, characterised in that the housing is formed in two parts joined together at mating end surfaces in the enlarged central region.

12. An HME device according to claim 11, characterised in that the mating end surfaces are inclined in opposite senses at an angle to the normal to an axis of the HME device.

13. An HME device according to claim 1, characterised in that opposite end surfaces of the HME element each form a shallow, concave, conical shape.

14. A heat and moisture exchange (HME) device comprising: a housing providing an inlet coupling, an outlet coupling and a transversely enlarged central region between the inlet and outlet couplings, the device including an HME element retained in the enlarged central region having opposite end faces spaced from respective inner opposing walls in the enlarged central region of the housing so that air can flow through the element across the entire surface of both faces, a hollow tubular sleeve extending axially through the HME element between the opposite end faces of the HME element in alignment with the inlet and outlet couplings, wherein the housing has at least in the enlarged central region a wall including foamed plastic material having a thickness adapted to provide thermal insulation of the housing around the HME element.

15. An HME device according to claim 14, further comprising a selectively openable valve in the tubular sleeve for reversing direction of air flow.

16. An HME device of claim 14, wherein the housing comprises two parts bonded together at respective mating end surfaces about the HME element.

17. An HME device of claim 14, wherein the foamed plastics material has a thermal conductivity of substantially 0.03 W/(m·K) or less.

18. A heat and moisture exchange (HME) device comprising: a housing providing an inlet coupling, an outlet coupling and a transversely enlarged central region between the inlet and outlet couplings, the device including an HME element retained in the enlarged central region having opposite end faces spaced from respective inner opposing walls in the enlarged central region of the housing so that air can flow through the element across the entire surface of both faces, a hollow tubular sleeve extending axially through the HME element between the opposite end faces of the HME element in alignment with the inlet and outlet couplings, wherein the housing has at least in the enlarged central region a wall including foamed plastic material having a thickness adapted to provide thermal insulation of the housing around the HME element, and wherein the tubular sleeve has respective flare ends, and wherein the inlet coupling and the outlet coupling have respective noses each extending into a corresponding one of the flare ends of the tubular sleeve to provide respective annular air flow passages around the outside of the respective noses.

\* \* \* \* \*